US012575757B2

(12) United States Patent
Seegerer

(10) Patent No.: US 12,575,757 B2
(45) Date of Patent: Mar. 17, 2026

(54) MAGNETIC RESONANCE TOMOGRAPHY SYSTEM WITH AN ADAPTED VENTILATOR HAVING AN AIR VOLUME AMPLIFIER

(71) Applicant: Siemens Healthhineers AG, Forchheim (DE)

(72) Inventor: Georg Seegerer, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 168 days.

(21) Appl. No.: 18/521,043

(22) Filed: Nov. 28, 2023

(65) Prior Publication Data

US 2024/0201292 A1 Jun. 20, 2024

(30) Foreign Application Priority Data

Dec. 14, 2022 (EP) ..................................... 22213380

(51) Int. Cl.
  *A61B 5/055* (2006.01)
  *G01R 33/31* (2006.01)
(52) U.S. Cl.
  CPC .............. *A61B 5/055* (2013.01); *G01R 33/31* (2013.01)
(58) Field of Classification Search
  CPC .. A61B 5/055; G01S 33/31; F04F 5/46; F04F 5/16; F04D 25/08; F04D 29/545; G01R 33/31
  See application file for complete search history.

(56) References Cited

U.S. PATENT DOCUMENTS

| | | | |
|---|---|---|---|
| 8,308,445 B2 | 11/2012 | Gammack et al. | |
| 2009/0060710 A1 | 3/2009 | Gammack et al. | |
| 2011/0236229 A1 | 9/2011 | Fitton et al. | |
| 2013/0045084 A1 | 2/2013 | Tu et al. | |
| 2017/0108563 A1* | 4/2017 | Mulder .............. | G01R 33/3804 |
| 2017/0227973 A1* | 8/2017 | Schnetter ............... | G01R 33/31 |
| 2022/0151494 A1* | 5/2022 | Biber ................... | A61B 5/0036 |
| 2022/0258212 A1* | 8/2022 | Schneider .............. | B08B 3/024 |

(Continued)

FOREIGN PATENT DOCUMENTS

| | | | | |
|---|---|---|---|---|
| CN | 105757870 A | * | 7/2016 | ............. F24F 7/007 |
| CN | 217785377 U | | 11/2022 | |
| DE | 202013105211 U1 | * | 12/2013 | ........... G01R 33/288 |

(Continued)

OTHER PUBLICATIONS

Jafari, M. et al.: "Numerical Investigation of Geometric Parameter Effects on the Aerodynamic Performance of a Bladeless Fan", in: vol. 55, Issue 1, Mar. 2016, pp. 223-233.

(Continued)

*Primary Examiner* — Colin T. Sakamoto
(74) *Attorney, Agent, or Firm* — Banner & Witcoff, Ltd.

(57) ABSTRACT

A magnetic resonance tomography system may include an adapted ventilator with an air exit. The adapted ventilator may include an airstream generator (e.g., with a motor), an air volume amplifier which is arranged at the air exit and/or includes the air exit, and an air line section which carries an airstream that is generated by the airstream generator to the air volume amplifier. The air volume amplifier may be configured to increase an air volume of the airstream that is carried via the air line section to the air volume amplifier, so that it outputs an airstream with increased air volume.

18 Claims, 4 Drawing Sheets

(56) References Cited

U.S. PATENT DOCUMENTS

2022/0397294 A1* 12/2022 Biber ..................... G01R 33/34

FOREIGN PATENT DOCUMENTS

| | | | | | |
|----|----------------|------|---------|--------------|-----------|
| EP | 4043900 | A1 * | 8/2022 | .............. | A61F 7/00 |
| GB | 2452490 | A | 3/2009 | | |
| GB | 2502106 | A | 11/2013 | | |
| WO | 2009030881 | A1 | 3/2009 | | |

OTHER PUBLICATIONS

Wikipedia: Druckverlust—https://web.archive.org/web/20210620112525/https://de.wikipedia.org/wiki/Druckverlust (Jun. 20, 2021).

theansweris27.com—Dyson's Air Multiplier with STAR-CCM+ ; https://web.archive.org/web/20210420031831/https://theansweris27.com/dysons-air-multiplier-with-star-ccm/ (Apr. 20, 2021).

Anutha M.A. et al.: "Design Development and Analysis of Bladeless Thruster", International Journal of Electrical, Electronics and Data Communication, ISSN(p): 2320-2084, ISSN(e):2321-2950, vol. 8, Issue 6, Jun. 2020.

Protecting Designs—Dyson files suit to enforce design and utility patents for its bladeless fan; https://www.protectingdesigns.com/81-dyson-files-suit-to-enforce-design-and-utility-patents-for-its-bladeless-fan (Jul. 19, 2022).

Philski's Blog—Who invented the first bladeless desktop fan, Dyson or a Japanese inventor in 1981? ; https://philski.tumblr.com/post/217993334/bladeless-fan-2 (Jul. 19, 2022).

* cited by examiner

MAGNETIC RESONANCE TOMOGRAPHY SYSTEM WITH AN ADAPTED VENTILATOR HAVING AN AIR VOLUME AMPLIFIER

CROSS REFERENCE TO RELATED APPLICATIONS

This patent application claims priority to European Patent Application No. 22213380.3, filed Dec. 14, 2022, which is incorporated herein by reference in its entirety.

BACKGROUND

Field

The disclosure relates to a magnetic resonance tomography system and to a use of an air volume amplifier and an adapted ventilator in and/or on a magnetic resonance tomography unit.

Related Art

During the operation of a magnetic resonance tomography unit (MRT), a strong magnetic field is normally generated inside an examination tunnel of the MRT. A not insubstantial magnetic leakage field, typically in the order of 10 mT to 100 mT, also prevails in the near surroundings of the MRT in this case. This magnetic leakage field can be disruptive to the deployment of electrical or mechanical components, in particular electric motors. The operating principle of said motors is usually based on the use of magnetic fields and yokes made of soft iron, i.e. they are magnetically soft. As a consequence, the functioning of these motors is usually impaired or they can even cease to function due to external magnetic fields greater than 10 mT or 20 mT. For example, an external magnetic field affects the iron laminations of the rotor and stator of the motor in such a way that, even if it essentially still functions, the motor often has higher losses and less power than without the external magnetic field. On the other hand, however, it is desirable to deploy electrical and mechanical components in precisely that region immediately surrounding the MRT, because the construction and assembly of the MRT at its place of use can be simplified and a space-saving installation can be achieved thereby.

Electric motors are required inter alia for ventilators, these being required for example to supply fresh air to a patient in the examination tunnel and for the cooling of (electronic) components or electrical circuits. The delivery of fresh air into the examination tunnel has the advantage firstly that the patient can be supplied with sufficient fresh air, thereby avoiding a feeling of motionless stuffy air which can aggravate feelings of claustrophobia. In addition to this, cooling of the patient by means of a gentle airstream of cool air can allow high-frequency pulses to be used at the upper power limit, so that the maximum possible power limit is essentially only limited by the permissible specific absorption rate (SAR) of the body tissue. This allows a better image quality to be achieved and possibly also allows the scan time to be shortened. Finally, the components that heat up during operation can usually be cooled more effectively by an airstream than by purely natural convection, for example. Electronic components are built into the patient couch, for example. They are therefore located in the vicinity of the examination region or field of view of the MRT and are consequently exposed to the full magnetic field strength of the MRT (for example 0.5 T-3 T for common devices).

Owing to the fact that motors are sensitive to the influence of external magnetic fields, it is necessary when positioning the ventilator motors to consider not only where an airstream is required but also where the magnetic leakage field is particularly low.

According to conventional techniques, this problem is usually dealt with for example by trying out various motors at various positions in order to arrive at a functioning arrangement of motors. In this case, the motors are placed in particular at positions in the near surroundings of the MRT where the size of the leakage field is somewhat smaller. Here, however, there is often competition in relation to the available space or structural space for various motors that are required as well as for other components which react sensitively to magnetic leakage fields. This solution therefore involves considerable testing overheads, in particular since it is often not known at the outset which components react in a particularly sensitive manner to external leakage fields. These issues mean that multiple installation scenarios have to be tested during development, in order to ensure that reliable functionality is established in series production. It is also often necessary to accept limitations with regard to the ventilators that are deployed, for example to deploy fewer than the optimum number of ventilators or to deploy ventilators which have less power or are less favorably positioned.

A further possibility, particularly if a structural space having a sufficiently low leakage field cannot be found, consists in screening the motor from the external magnetic field by means of housings made of iron plate. Such housings made of iron plate are however very heavy and also cause considerable mechanical stresses in the magnetic leakage field.

Finally, ventilator motors can also be positioned far away from the MRT or the MR magnet, i.e. at a distance of more than a meter and/or in an adjoining room which does not contain the MR magnet, for example. In this case, an airstream can be carried to the desired locations via a hose line or a tube. However, this has the disadvantage that hoses of large diameter (often 10 cm or more in diameter) are required. The use of such wide hoses increases the time needed for the installation and requires additional space in which to lay the hoses. For example, in the case of a patient ventilator that is used to provide fresh air in the treatment tunnel, a hose with if possible a diameter of at least 50 mm is deployed, said hose transporting an airstream to an air outlet at one end of the treatment tunnel. The space between the plastic cover of the MRT and the magnet is however limited and it is therefore sometimes necessary to use a hose with a somewhat smaller diameter. It is therefore necessary to compensate by using a significantly stronger ventilator motor in order to achieve a required air flow rate. In conventional designs of the magnet and the plastic cover it is sometimes not possible for reasons of space, and owing to very large magnetic leakage fields, for the ventilator to be placed directly at a desired location of the air outlet.

Electronic components which are arranged in or at the examination region, for example on the patient couch, can however generally only be incorporated if their heat-generating power loss is low enough to be dissipated by natural convection. It is therefore often necessary to accept restrictive compromises, for example with regard to the quality and reliability of the components or the measurement results.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
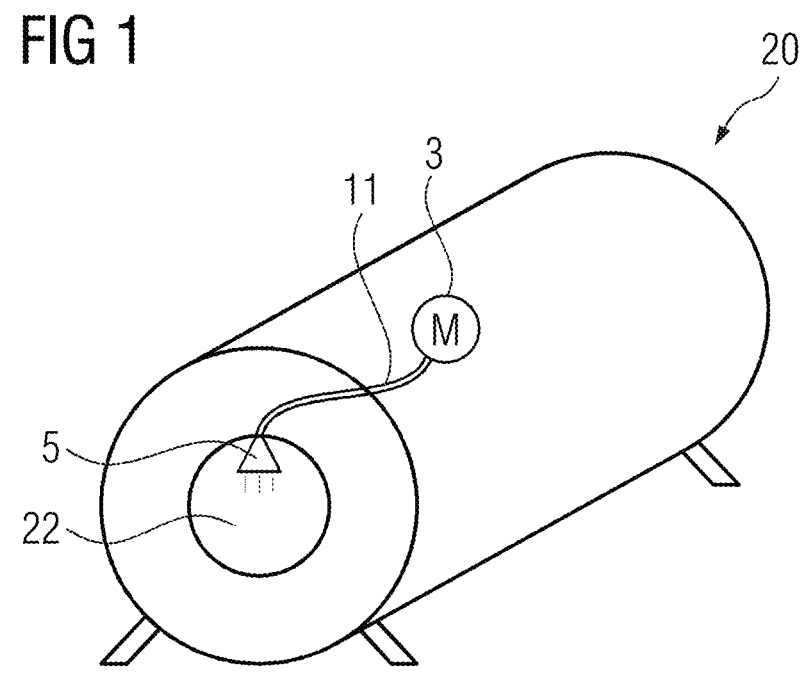
FIG. 1 shows a perspective view of an example magnetic resonance tomography system.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to provide a magnetic resonance tomography system in which the problems cited above are solved more effectively and in particular ventilation can be incorporated with greater positional flexibility despite the presence of magnetic leakage fields.

This object is achieved by the present disclosure, such as by, for example, a magnetic resonance tomography system, an adapted ventilator, a use of an air volume amplifier, and a use of an adapted ventilator.

According to a first aspect of the disclosure, provision is made for a magnetic resonance tomography system (MRT system) comprising an adapted ventilator with an air exit, said adapted ventilator comprising an airstream generator, in particular with a motor, an air volume amplifier which is arranged at the air exit and/or comprises the air exit, and an air line section which carries an airstream that is generated by the airstream generator to the air volume amplifier, the air volume amplifier being so configured as to increase an air volume of the airstream that is carried via the air line section to the air volume amplifier, so that it outputs an airstream with increased air volume. The term "adapted ventilator" signifies that the ventilator is adapted to the fact that magnetic leakage fields generated by the MRT are present in the surroundings of the MRT during operation. In particular, the ventilator is adapted in that it comprises the air volume amplifier which is arranged at the air exit or comprises the air exit. The air volume amplifier can be so configured as to comprise in particular an aerodynamic design or an aerodynamic system, whereby the airstream emerges from the air exit of the air volume amplifier in such a way that surrounding air is entrained and amplifies the air volume thus. The design of the air volume amplifier and/or the connection of the air line section to the air volume amplifier, and optionally the design of the airstream generator, can be provided correspondingly as described in the document US 2009/060710 A1, for example. The air volume amplifier can be developed in particular as a "bladeless fan." In an exemplary embodiment, the air volume amplifier itself may comprise the air exit of the adapted ventilator, i.e. the air exit of the air volume amplifier can correspond to the air exit of the adapted ventilator. It is alternatively also conceivable to provide a further, separate air exit of the adapted ventilator, behind the air volume amplifier in a flow direction, in particular in addition to the air exit of the air volume amplifier. In this case, the air volume amplifier can be arranged at the air exit of the adapted ventilator. A separate air exit can be configured for example to redirect, to focus or otherwise to influence the airstream with amplified air volume. The airstream generated thereby with increased air volume can have in particular a lower speed than the airstream which is carried to the air volume amplifier.

The airstream generator can be based on the principle of a ventilator with rotor blades which are driven by the motor, said rotor blades being configured in particular such that they generate the airstream when they are operated by the motor, said airstream being carried via the air line section to the air volume amplifier. The air line section can be an air line in the form of a hose or a tube. By virtue of the air line section, it is possible to arrange the airstream generator separately from the air volume amplifier. In particular, the airstream generator and in particular the motor of the airstream generator can be arranged at a position which, during operation of the MRT, is exposed to a weaker magnetic field than the position at which the air volume amplifier is arranged. In other words, a spatial separation of the motor and the air exit can be achieved. This means that it is advantageously easier when designing the MRT system to ensure that the motor and even the whole air volume generator including its possibly moving parts such as for example rotor blades can be arranged at a location with a low magnetic field strength, while at the same time only a small air volume has to be transported from the airstream generator to the air exit. By comparison, if a large air volume had to be transported via the air line section, in particular the entire air volume that is output at the air exit, this would result in considerably higher pressure losses and flow losses. An increase in the air volume that must be conveyed per time unit results in an increased flow speed. Assuming a laminar flow in the air line section, this increased flow speed results in flow losses which rise quadratically with the speed. By virtue of the lower flow losses, it is consequently possible in the case of the inventive MRT system to use a slightly less powerful motor, such that said motor can be more economical in terms of both procurement and operation. Alternatively, the option also exists to reduce the diameter of the air line section, whereby less structural space is required and therefore fewer compromises must be accepted when configuring the MRT system. It is also possible to use a longer air line section, whereby the motor can be arranged in a region with a lower magnetic field strength, in particular in a region which is further away from the magnet of the MRT and/or the location of the air exit.

According to an exemplary embodiment, the air volume amplifier is made from a non-magnetic or non-magnetizable material and/or a non-conductive material, in particular from a synthetic material. It is thereby advantageously possible to ensure that the physical functioning of the MRT, which requires strong magnetic fields and electromagnetic high-frequency pulses, is not substantially impaired by interaction with magnetizable components of the air volume amplifier. It would otherwise be possible for example for electrical currents to be induced in conductive elements of the air volume amplifier due to gradient pulses of the MRT. It is also possible by means of this exemplary embodiment to ensure that no magnetic forces or only negligible magnetic forces act on the air volume amplifier. According to one or more embodiments, it is possible to allow placement near or in the examination region or field of view. "Near" in this context can signify in particular that a distance of less than 50 cm is envisaged. For example, it can be conceivable to provide the air exit directly in the interior of an examination tunnel of the MRT, in which the full field strength of the generated magnetic field prevails during operation of the MRT.

According to an exemplary embodiment, the air volume amplifier is configured to passively increase the air volume by virtue of its geometric structure. The term passive in this case is intended to signify in particular that the air volume is increased without active movement of individual components of the air volume amplifier and/or without actively driving the air volume amplifier. In particular, the air volume amplifier does not comprise or need its own motor. As a result of the structure, in particular by omitting moving components and/or omitting a motor, it is advantageously possible to reduce any interaction with the magnetic field of the MRT. In particular, it is thereby possible to prevent an induction of eddy currents generated by the magnetic field. The air exit of the air volume amplifier can be so configured as to fully or partially enclose a convex figure. In particular, a viewing direction towards the direction of the emerging airstream with increased air volume is assumed in this case. In an exemplary embodiment, the air exit may be configured as a complete or partially open oval or polygon. The oval can be in particular an ellipse or a circle. In an exemplary embodiment, the polygon can be a quadrilateral, in particular a rectangle, and the corners of the quadrilateral can optionally be rounded. A partial enclosure, or being open in this case, may include an enclosure or being open by more than 50% and less than 95%, in particular by means of a continuous air exit. Particularly efficient air amplification can be achieved thereby. The shape of the air exit can be adapted to the geometric conditions of the respective field of deployment of the air volume amplifier and the MRT system. Provision can be made for the connection of the air line section to the air exit to be arranged and/or attached laterally relative to the air exit or the convex figure, in particular substantially perpendicular to the area of the convex figure. "Substantially" in this case signifies in particular having an angular deviation of no more than 15°. In this case, the convex figure or the area that is fully or partially enclosed by the air exit is open, in particular towards both its front side and its rear side. In an exemplary embodiment, the air exit may be configured such that when the air emerges, a differential pressure is generated between the two sides of the convex figure and/or between the side into which the amplified airstream flows and the opposite side thereto. It is thereby advantageously possible for surrounding air to be entrained with the airstream that is output, whereby the airstream can be amplified. The rear side of the air exit, in particular in a cross-sectional view perpendicular to the flow direction of the emerging airstream, can be so developed as to be rounded or curved. In particular, the external extent of the cross-sectional view can approximate the cross section of the wing of an airplane. In this case, the air exit can be arranged at the thicker end of the cross section and point in a direction which deviates from the direction of the tapering part by an angle of 5° to 60° towards an interior of the convex figure. The detailed structure of the air volume amplifier can be fundamentally similar to the principles that are known from the prior art. These are described and explained for example in the publication by Mohammad Jafari et al.: "Numerical investigation of geometric parameter effects on the aerodynamic performance of a Bladeless fan", Alexandria Engineering Journal (2016) 55, 223-233; http://dx.doi.org/10.1016/j.aej.2015.11.001 and in the publications of Anutha M A et al.: "Design Development and Analysis of Bladeless Thruster", International Journal of Electrical, Electronics and Data Communication, ISSN(p): 2320-2084, ISSN(e):2321-2950, Volume 8, Issue 6, June 2020.

According to an exemplary embodiment, the air exit comprised by the air volume amplifier is configured to be annular or in the shape of an annular section. Additionally or alternatively, the air volume amplifier has an air-guiding annulus or annular section with air exit openings through which air is output in a direction having a directional component that is perpendicular to the annular plane, in particular in a direction perpendicular to the annular plane or in a direction that deviates by no more than 30° from the direction perpendicular to the annular plane. The air exit openings can also be combined to form a continuous opening that extends around the annulus. In this case, the annulus does not necessarily have to be circular in design, and can be generally oval or elliptical. A structure in the form of an annulus or annular section can be particularly favorable for achieving air amplification. In particular, the annulus or annular section fully or partially encloses a convex figure as described above.

According to an exemplary embodiment, the airstream generator is arranged in a first region which, when the magnetic resonance tomography system generates a magnetic field during operation, has a lower magnetic field strength than a second region in which the air volume amplifier is arranged. This embodiment makes it possible to exploit the advantage that, due to the limited air volume to be conveyed through the air line section when using the inventive MRT system, a flexible arrangement of the airstream generator or the motor can be achieved, since the general susceptibility of motors to external magnetic fields can be compensated by means of suitable positioning. The first region can have a distance of at least 1 m from the main magnet of the MRT and/or can be arranged or attached in a region of the MRT system which has a lower magnetic field strength than all of the regions of the MRT system which are situated outside the main magnet, and are less than 1 m away from the main magnet, on average. For example, provision can be made for the first region to be situated in a different room than the main magnet and/or the examination tunnel of the MRT. Alternatively or additionally, the first region can be arranged in a central region viewed in a longitudinal direction of the examination tunnel, to the side and outside the main magnet, in particular in the vicinity of the outer wall and/or at an outer wall of the MRT. The central region can be in particular the region which is situated in the central third of the examination tunnel viewed in a longitudinal direction of the examination tunnel. The outer wall can be in particular a side wall and/or a floor wall of the MRT. "In the vicinity of the outer wall" can signify in particular that the first region has a maximum distance from the outer wall which is no greater than the distance from the front or rear end of the examination tunnel as viewed in a longitudinal direction of the examination tunnel. As a rule, the magnetic leakage field of the MRT system is advantageously lower in the central region or central third than at other locations to the side of the main magnet. Alternatively or additionally, the central region can be arranged in a lower kick space of the MRT. As a result of the more favorable positioning of the motor permitted thereby, the choice of the motor in particular can be less restrictive because it is not as important to ensure that the motor is resistant to external magnetic fields.

According to an exemplary embodiment, the air volume amplifier is configured to amplify the air volume at least 5-fold (e.g., 500%), preferably at least 10-fold, particularly preferably at least 15-fold. The possibility of realizing such an amplification is set forth by Mohammad Jafari et al. in "Numerical investigation of geometric parameter effects on the aerodynamic performance of a Bladeless fan", Alexandria Engineering Journal (2016) 55, 223-233. It is therefore advantageously possible by means of amplifying the air volume directly at the location where the airstream is required, i.e. in particular at or in front of the air exit, to provide for the air volume which is carried through the air line section to be significantly reduced. It is thereby possible to use for example an air line section having a smaller diameter. For example, in the case of an amplification to at least 10-fold, it is conceivable both to use an air line section having a smaller diameter and to operate a motor with lower power, since the flow losses are lower when the air volume that is carried is lower. It has been shown that in the case of a reduction to $\frac{1}{15}$ of the transported air volume, this being possible in the case of an intended amplification to 15-fold, an estimated reduction to approximately $\frac{1}{225}$ is possible. This means that it is alternatively or additionally possible to provide a longer air line section, for example. The degree of freedom and possible options in respect of the structure and design of the MRT system are increased thereby. In the case of a 15-fold amplification, it has been shown that in order to compensate, the pressure of the air volume which is carried through the air line section must be approximately five times greater than if the air volume is carried directly in greater volume to the air exit, in order to allow passive amplification. However, the advantages which are obtained as a result of the lower friction losses, and apply quadratically in the energy balance, generally far outweigh this limitation. For example, provision can be made to plan for a maximum air amplification of 30-fold, in particular in order to limit the higher pressure that is required.

According to an exemplary embodiment, the airstream generator is configured to input the airstream into the air line section with a pressure of 80 Pa to 500 Pa, preferably 100 Pa to 350 Pa, particularly preferably 150 Pa to 300 Pa. If the air volume amplifier works in a passive manner according to an exemplary embodiment, the energy that is required for the amplification of the airstream must derive from the energy of the airstream that is supplied through the air line section. This can be effected in particular by virtue of the airstream supplied through the air line section having a higher pressure than a corresponding airstream which does not have to be amplified. As a result of the increased pressure, the available airstream can have enough energy to entrain sufficient surrounding air during the air amplification and thereby amplify the airstream. A pressure of 100 Pa to 350 Pa can be generated with relative ease by common motors and ventilators, in particular because a smaller air volume is used. At a generated pressure of 150 Pa to 300 Pa in particular, as a result of the amplification that is then possible, the air volume that is used can be so significantly reduced that only a sufficiently small fraction of the air volume which is required at the air exit has to be carried through the air line section, whereby flow losses in particular can be significantly reduced. The specified pressure ranges in this case are not intended to signify that the motors cannot also be capable of optionally inputting lower pressures. For example, it can be possible to adjust the motors downwards. This can be expedient if, for example, only a limited cooling capacity is required at the time, in particular in connection with a self-regulating cooling capacity.

According to an exemplary embodiment, the airstream generator is a diagonal-flow fan or a radial-flow fan, or is developed as a diagonal-flow fan or radial-flow fan. In particular, diagonal-flow fans and radial-flow fans are particularly suitable for generating a high differential pressure with a simultaneously low air flow rate. They can therefore be particularly suitable for the adapted ventilator according to the disclosure, in particular if only a limited air volume is carried through the air line section.

According to an exemplary embodiment, the magnetic resonance tomography system comprises an examination tunnel with a tunnel entrance, the air volume amplifier being arranged at the tunnel entrance and being oriented such that the amplified airstream is directed into the examination tunnel, in particular substantially along the longitudinal axis of the examination tunnel, or is oriented such that the amplified airstream is directed out of the examination tunnel. The tunnel entrance can be in particular a rear tunnel entrance opposite the entrance at which a patient couch is arranged and/or at which a patient is introduced, and/or the tunnel entrance can be a front tunnel entrance which corresponds to the entrance at which a patient couch is arranged and/or at which a patient is introduced. The tunnel entrance can be (temporarily) closed by a sealing means and nonetheless designated a tunnel entrance. Accordingly, it can be made possible to supply a patient with sufficient fresh air. An arrangement at a rear tunnel entrance can advantageously allow the patient to be introduced with fewer obstructions if applicable and further components which may be positioned at a front tunnel entrance (for example a display, an operating panel, a cross laser for positioning, a mechanism for the docking of a patient couch, etc.) possibly require the space at the front tunnel entrance. An arrangement at a front tunnel entrance can have the advantage that maintenance and adjustment of the airstream amplifier can be performed more easily and more quickly if necessary. An orientation of the airstream into the examination tunnel can have the advantage that the whole amplified airstream can be used for the ventilation. An orientation of the airstream out of the examination tunnel can have the advantage that an airstream (which is smaller) is drawn from the tunnel (corresponding to the volume of air that is added by the airstream amplification), such that a ventilation effect can still be achieved in the examination tunnel. It is therefore possible, if applicable, to prevent a faster airstream from being directed into the face of a patient.

This can be achieved by means of the inventive adapted ventilator, wherein at the same time the motor of the ventilator can be positioned further away from the tunnel entrance. This is advantageous firstly because little space is available at the tunnel entrance or in the vicinity of the tunnel entrance, in particular because other components must also be positioned there, for example at least a gradient coil. Secondly, the magnetic field at that location during operation of the MRT is usually very strong or too strong for the operation of normal motors. The air volume amplifier may be arranged within the examination tunnel at the tunnel entrance.

According to an exemplary embodiment, the air exit comprised by the air volume amplifier is arranged around a perimeter of the tunnel entrance and in particular surrounds the tunnel entrance in an annular or partially annular manner. In particular, the air exit comprised by the air volume amplifier can be configured to be annular or in the shape of an annular section. The shape of the air exit or the annular shape of the air volume amplifier may be adapted to the shape of the tunnel entrance. The air exit, which is partially annular or configured as an annular section, may be so developed as to be at least half of an annulus or at least three quarters of an annulus. A complete annulus can allow particularly efficient air amplification at the same time as particularly uniform air distribution. A partial annulus can be advantageous in order to ensure that sufficient space is available for further components, for example connection cables of the gradient coil. In an exemplary embodiment, partially annular means that the annular shape extends over a maximum of 95% of a complete annulus. In another embodiment, partially annular means that the annular shape extends over a maximum of 90% of a complete annulus. Accordingly, the shape of the air amplifier or the air exit of the air amplifier can advantageously be adapted to the tunnel entrance. This allows a particularly uniform airstream to be generated, which can be particularly pleasant for a patient. In this case, the fact is exploited that an air amplifier which is annular or adapted to the tunnel entrance can generate an airstream that is uniformly distributed over the whole or nearly the whole cross section of the tunnel. Provision can be made in particular for the connection of the air line section to the air exit to be arranged or fixed laterally relative to the air exit. It is thereby advantageously possible to ensure that the tunnel entrance is not substantially blocked by the adapted ventilator. As a result of the uniform airstream, it is moreover possible to ensure that the airstream need not be locally set in a manner which is unpleasantly strong for the patient. This is particularly relevant because the patient, depending on the body region being examined, is placed at various positions in the examination tunnel. An airstream which is less uniform, as provided by ventilators according to the prior art, has the disadvantage here that it must necessarily be particularly strong at some places, in particular near to the air exit, in order to effectively ventilate places which are also more distant.

According to an exemplary embodiment, the magnetic resonance tomography system comprises a patient couch which is configured to be moved at least partially into an examination region of the magnetic resonance tomography system, the air volume amplifier being arranged and attached to the patient couch such that, when the patient couch is moved into the examination region, it is moved into the examination region with the patient couch. The examination region can be situated in particular in the examination tunnel of the MRT. The patient couch can be moved in particular from an external position outside the examination tunnel into an examination position within the examination tunnel. Accordingly, it is also possible to output an airstream within the examination region, for example in order to cool components in the examination region. According to an exemplary embodiment, the patient couch comprises at least one electronic component, in particular at least one receiving coil, the air volume amplifier being arranged in such a way that the amplified output airstream is mainly (e.g., substantially) directed at the at least one electronic component.

"Substantially" according to an exemplary embodiment can be understood to mean that at least 85% of the airstream is directed at the component. In the examination region during operation of the MRT, the full strength of the MRT magnetic field is prevalent, for example in the range from 0.5 T to 3 T or even more. A ventilator according to the prior art cannot usually be used here. However, by means of the adapted ventilator design described herein and in particular by means of a spatial separation of motor and air exit, the output of an airstream can advantageously also be made possible in the examination region. By means of the air amplification, it can be ensured in particular that only a small air volume has to be carried to the air exit.

According to an exemplary embodiment, the magnetic resonance tomography system comprises an examination tunnel with a tunnel entrance via which the patient couch can be moved into the examination region, the examination region being arranged in the examination tunnel, the magnetic resonance tomography system comprising a support element which is arranged in front of the tunnel entrance, the patient couch being supported by resting on the support element when it is moved out of the examination tunnel, the air current generator being arranged outside on the support element or being integrated in the support element, and the air line section between the airstream generator and the air volume amplifier being so developed as to be flexible, in particular as an air hose. The airstream generator may be arranged at a foot end of the support element and/or in a half of the support element which faces away from the tunnel entrance. The magnetic leakage field at the foot end is usually relatively low, typically in the order of 5 mT or less. At this position, the motor is also sufficiently far from the examination region to be able to rule out any significant influence on a measurement. A motor in the examination region or in the vicinity of the examination region would however be disadvantageous because moving metal parts of the motor would, owing to their conductivity, result in eddy currents which could disrupt the homogeneity of the magnetic field and therefore lead to imaging errors. As a result of the air amplification at the air exit, it is possible to use a particularly thin air line section or air hose, whereby only relatively little structural space is necessary. For example, a diameter of the air line section can be limited to a maximum of 3 cm. With this diameter, integration into existing systems can be enabled without having to make substantial changes to the design of the mechanism and/or the electronics of the patient couch.

A further aspect of the disclosure relates to a use of an air volume amplifier, in particular an air volume amplifier as described herein, and/or of an adapted ventilator as described herein, in and/or on a magnetic resonance tomography unit, in particular for the purpose of generating an amplified airstream and/or cooling at least one component of the magnetic resonance tomography unit. All of the advantages and features of the magnetic resonance tomography system can be transferred analogously to the use of an air volume amplifier and vice versa.

A further aspect of the disclosure relates to a use of an adapted ventilator, in particular an adapted ventilator as described herein, for the purpose of cooling at least one component of a magnetic resonance tomography unit and/or for the purpose of ventilating an examination region of the magnetic resonance tomography unit, the adapted ventilator comprising an airstream generator with a motor, an air volume amplifier which is arranged at the air exit and/or which is the air exit, and an air line section which carries an airstream that is generated by the airstream generator to the air volume amplifier, the air volume amplifier being so configured as to increase an air volume of the airstream that is carried via the air line section to the air volume amplifier, so that it outputs an airstream with increased air volume. All of the advantages and features of the magnetic resonance tomography system and the use of an air volume amplifier can be transferred analogously to the use of an adapted ventilator and vice versa.

Figure 2:
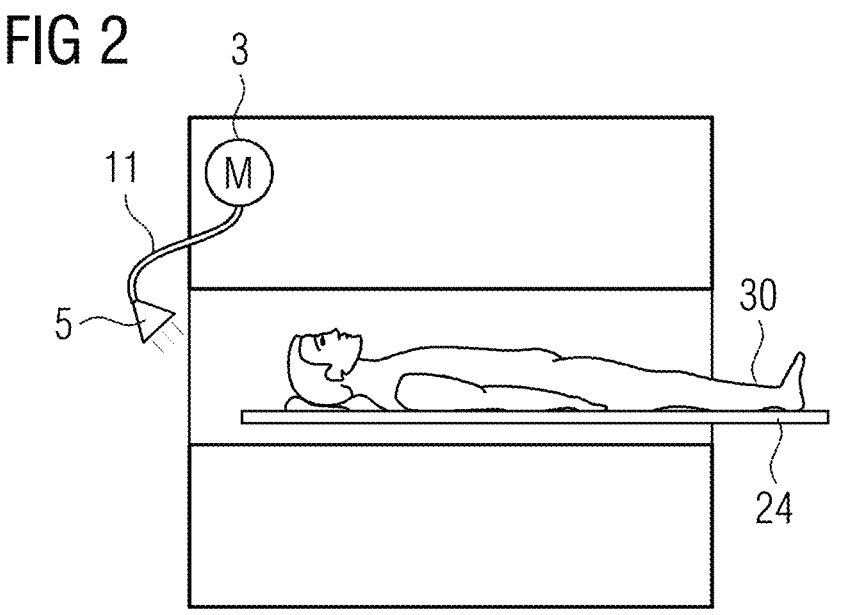
FIG. 2 shows a sectional view of an example magnetic resonance tomography system.

FIGS. 1 and 2 show a magnetic resonance tomography system according to the prior art in a perspective view (FIG. 1) and in a sectional side view (FIG. 2). The air exit 5 is arranged at a rear end here, in the upper region of the examination tunnel 22 of the magnetic resonance tomography unit (MRT) 20 in which the examination region is located. In this case, a motor 3 pushes air through a hose 11 to the air exit 5. The motor 3 is arranged outside the MRT magnet at the MRT. On one hand, the choice of motor 3 is restricted in this case because the motor must be to some extent resistant to external magnetic fields. On the other hand, the positioning of the motor 3 is also restricted because it must be positioned at a location with the lowest possible magnetic field strength while at the same time being positioned relatively near to the air exit 5, since the length of the air hose 11 is limited in order that the total required air volume can still pass through the air hose 11. In respect of the positioning, competition with other components is a particular consideration. The motor here is arranged to the side and towards the top of the magnet in the vicinity of the rear end of the examination tunnel 22. The motor 3 in this case is usually placed outside the MRT magnet but still within a plastic cover of the MRT 20. The air hose 11 has a length of approximately 50 cm from the connection at the motor 3 to the air exit 5 and a diameter of approximately 50 mm to 90 mm. The motor 3 must not be positioned directly at the air exit 5, firstly because there is little space there and other components also have to be placed there (for example gradient coil), secondly because an excessively strong leakage field of the large MRT magnet prevails, and thirdly because alternating magnetic fields can be generated whose interaction with the motor 3 would disrupt both the motor 3 and MRT measurements. If the motor 3 were to be positioned too close to the examination region, eddy currents would be induced in the metallic parts of the motor 3. These would disrupt the magnetic field in the field of view which is located in the examination region and/or heat the motor 3 to an unacceptable extent or otherwise impair the functioning thereof. Moreover, placement too close to the field of view or to the examination region could result in the motor 3 with its (rotating) magnetic field causing fluctuations in the magnetic field at the location of the field of view, thereby disrupting the measurements. A further disadvantage of this embodiment according to the prior art is that in order to be able to generate a sufficiently strong airstream in the whole tunnel, in order to avoid stuffy air, a relatively high flow speed is required at the air exit 5. This can be unpleasant for a patient 30 if it is necessary to examine a body region (for example thorax, diaphragm) whose positioning in the field of view means that the head of the patient 30 lies directly in the vicinity of the air exit 5 where the airstream is particularly strong.

Figure 3:
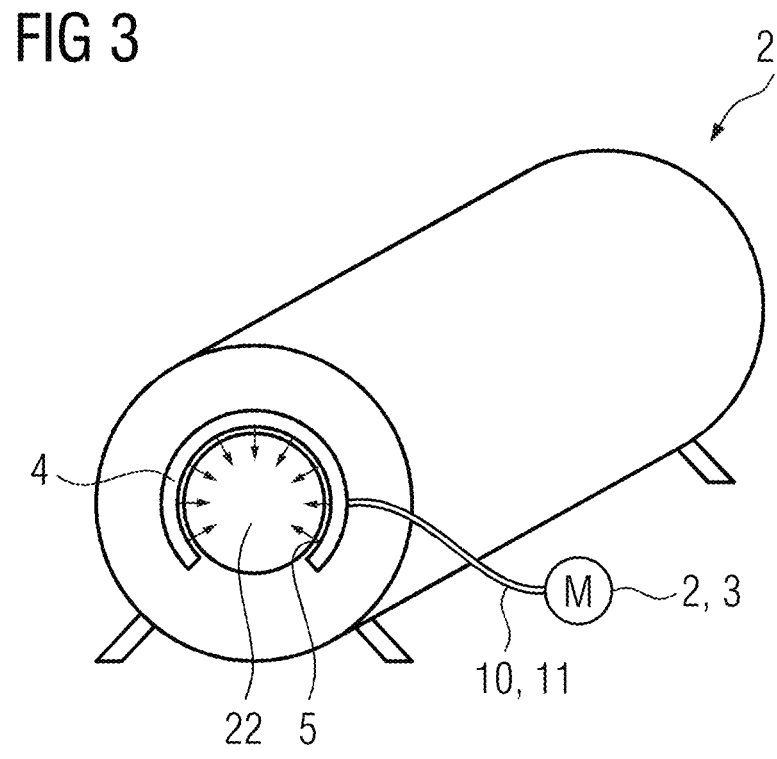
FIG. 3 shows a perspective view of a magnetic resonance tomography system according to an exemplary embodiment of the disclosure.
Figure 4:
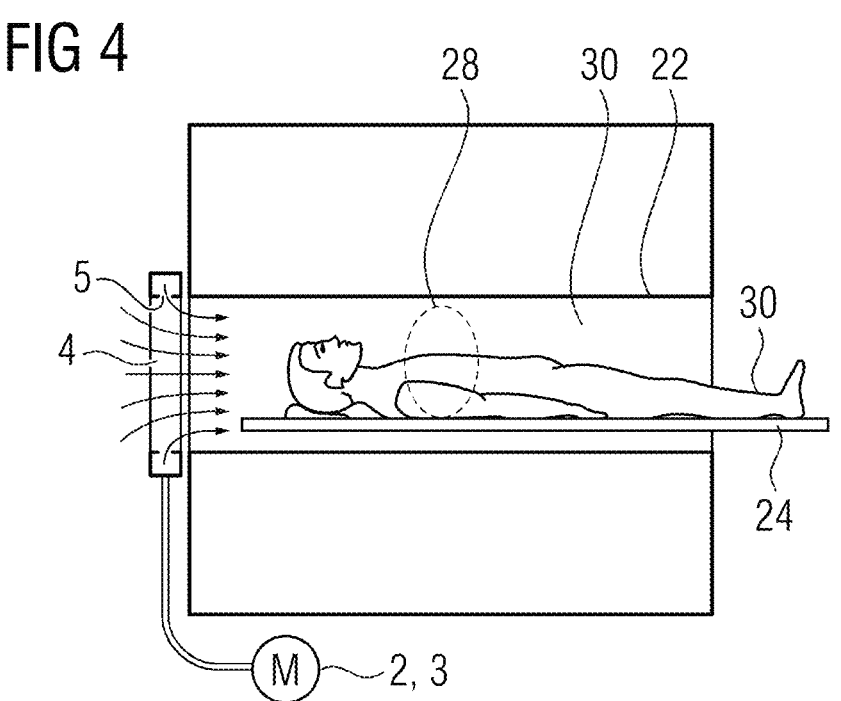
FIG. 4 shows a sectional view of a magnetic resonance tomography system according to an exemplary embodiment of the disclosure.

FIGS. 3 and 4 show a magnetic resonance tomography system according to an exemplary embodiment of the disclosure in a perspective view (FIG. 3) and in a sectional side view (FIG. 4). The magnetic resonance tomography unit (MRT) 20 has an examination tunnel 22 in which is situated an examination region and at whose tunnel entrance is arranged an air volume amplifier 4 according to the disclosure. The MRT 20 may also be referred to as magnetic resonance (MR) scanner 20. The field of view 28, i.e. the region in which the magnetic resonance tomography unit can generate an image, is situated in the examination region and by way of example here consists of a sphere having a diameter of 40 cm in the center of the examination tunnel. In the illustration according to FIG. 4, an image can be made of the thorax of a patient 30.

The air volume amplifier 4 here is arranged around the rear tunnel opening and is oriented such that the airstream amplified thereby is directed into the examination tunnel 22. The air volume amplifier 4 is arranged around a perimeter of the tunnel entrance and is configured to be annular in accordance with the shape of the tunnel entrance, this annulus being interrupted in the lower region such that the air volume amplifier 4 surrounds the tunnel entrance in a partially annular manner. That part of the annular extent which is left open can be used to allow space for further components, in particular connection cables of the gradient coil. Alternatively, the air volume amplifier can be developed as a complete annulus, whereby air volume amplification and a uniform air flow can be achieved even more efficiently.

An airstream generator 2 with a motor 3 is arranged in a region where the magnetic field is relatively low during operation of the MRT 20, in particular lower than at the tunnel entrance. Moreover, the airstream generator 2 can be placed at a location where there is less competition with various other components, in particular with electronic components which are intended to be mounted to the side of the magnet and easily accessible, for the limited available structural space. The airstream generator 2 may comprise a fan which is configured to provide a high differential pressure with a low air flow rate, for example, a diagonal-flow or radial-flow fan.

Air that is generated by the airstream generator 2 is carried through an air line section 10 (e.g., an air hose 11) to the air volume amplifier. Since only a fraction, for example approximately $\frac{1}{15}$, of the total airstream output at the air exit 5 must be conveyed through the air line section 10, this can be longer and thinner. For example, the air line section 10 can be 2 m to 3 m long and have a diameter of 40 mm to 50 mm.

In an exemplary embodiment, the airstream from the air volume amplifier 4 remains close to the wall of the examination tunnel 22, while the air that is entrained by the amplification of the airstream occurs moves more centrally. In this way, there is no point of the tunnel cross section at which an air flow is significantly faster than at other points. Local regions of greater air flow which could blow unpleasantly into the face of the patient 30 can advantageously be avoided thus. At the same time, a particularly uniform ventilation can be ensured. This can be advantageous in particular because the examination tunnel is relatively narrow as a rule, for example in the range of 60 cm to 80 cm in diameter in cross section, and it is possible that not much space remains for the ventilation when a patient 30 is lying in the examination tunnel 22. Particularly in the case of longer examination times (for example up to 20 minutes), good ventilation is therefore desirable and can be achieved particularly efficiently according to the disclosure.

Figure 5:
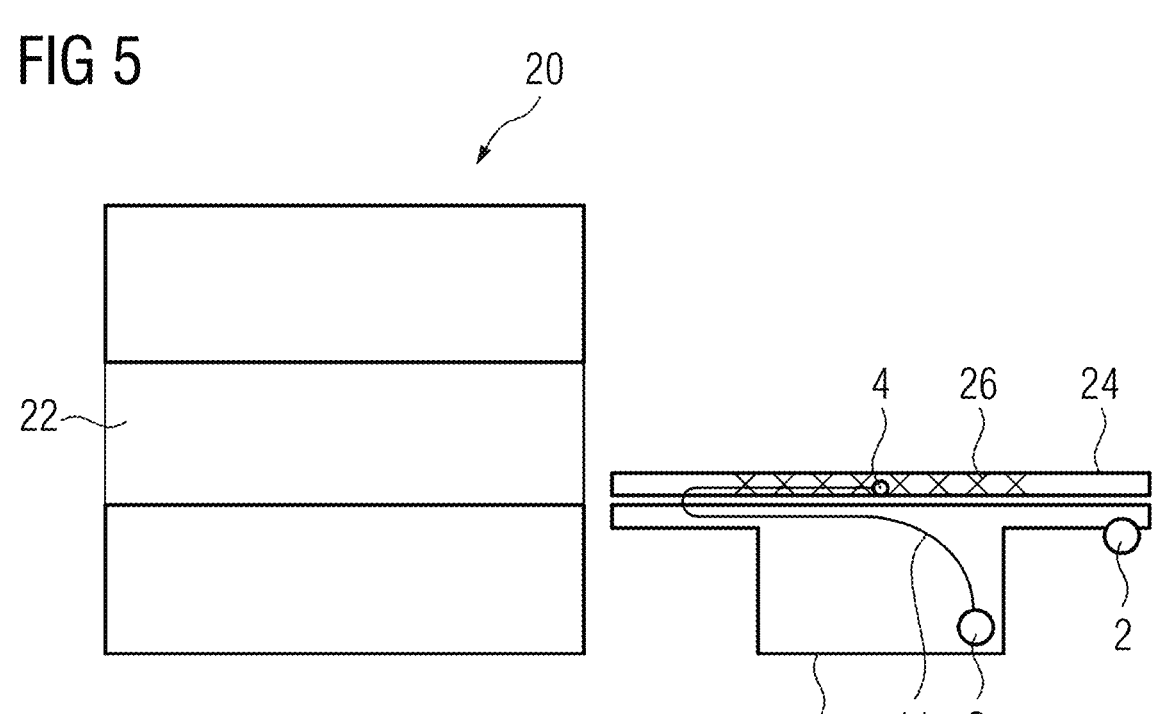
FIG. 5 shows a sectional view of a magnetic resonance tomography system, with a patient couch which has been moved out, according to an exemplary embodiment of the disclosure.
Figure 6:
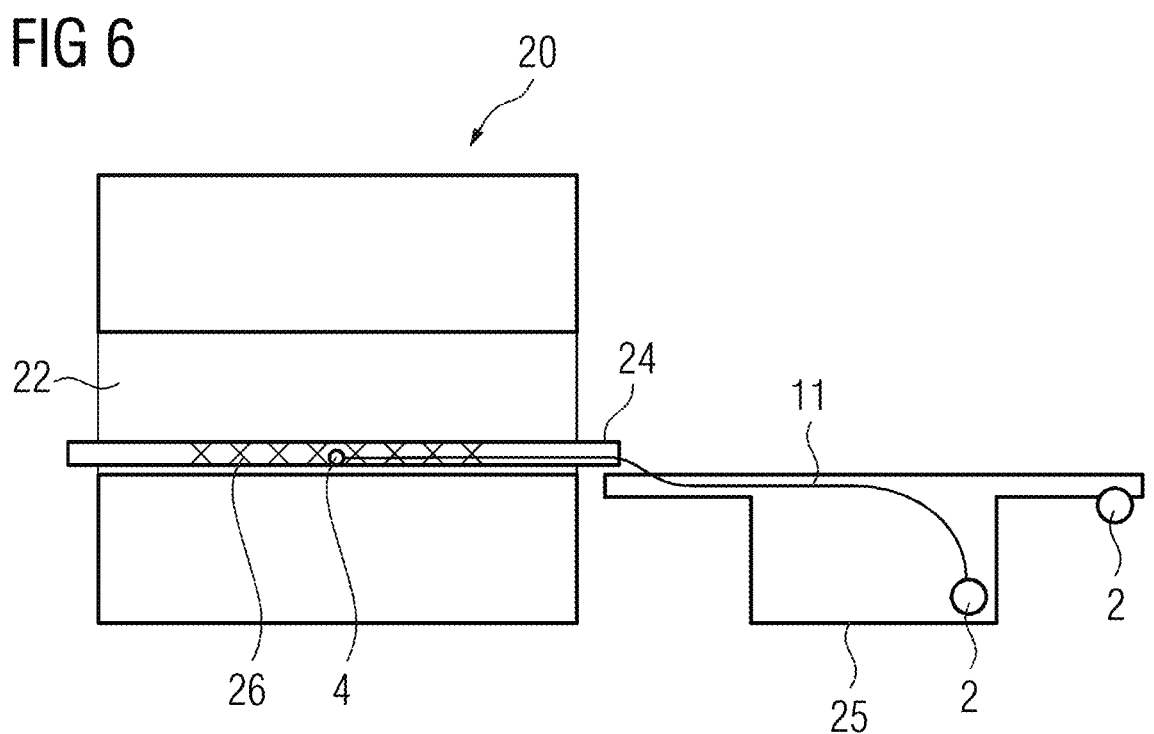
FIG. 6 shows a sectional view of a magnetic resonance tomography system, with a patient couch which has been moved in, according to an exemplary embodiment of the disclosure.

FIG. 5 shows a sectional view of a magnetic resonance tomography system according to an exemplary embodiment of the disclosure, with a patient couch 24 which has been moved out, while FIG. 6 shows a sectional view of the magnetic resonance tomography system with a patient couch 24 which has been moved in. The diameter of the examination tunnel can be in the range of 60 cm to 80 cm, for example. The length of the MRT magnet can be less than 2 m, for example.

The patient couch 24 is configured to be moved into an examination region in the examination tunnel 22 of the MRT system. The patient couch 24 is movable and therefore a patient 30 can lie on the patient couch 24 outside the examination tunnel (FIG. 5) and can then be moved into the tunnel of the magnet (FIG. 6). The air volume amplifier 4 may be attached to the patient couch 24 such that, when the patient couch 24 is moved into the examination tunnel 22, it is moved into the examination tunnel 22 with the patient couch 24.

The patient couch 24 may comprise a plurality of receiving coils 26 which are installed in the patient couch, and the air volume amplifier 4 is so arranged that the airstream amplified thereby is directed primarily at the receiving coils 26. The receiving coils 26 are used in particular to make images of the back region of the patient 30 (so-called "spine coils"). The approximate position of the receiving coils is marked with crosses. Amplifiers (low noise amplifier=LNA) are installed close to the receiving coils 26 in each case. In conventional solutions, it was necessary to rely on air convection for the purpose of cooling the coils and the amplifiers, since ventilation in the tunnel 22 was not possible. It is alternatively also conceivable to install other components, in particular other electronic components, which were previously unusable due to for example lack of adequate cooling but can now be cooled by means of the adapted ventilator. Electronic components can be equipped with smaller heat sinks and/or more powerfully designed than before, for example, this being possible in particular because they can be cooled by means of the adapted ventilator with an airstream instead of merely via convection.

A support element 25 is arranged in front of the tunnel entrance of the examination tunnel 22 and supports the patient couch 24 in that this rests on the support element 25 when it is outside the examination tunnel (as per FIG. 5). The airstream generator 2 in this exemplary embodiment is arranged externally at the support element 25 or is integrated in the support element 25. In this illustration, two positions for the airstream generator 2 are marked where the airstream generator could be arranged either alternatively or, in the case of multiple adapted ventilators, simultaneously. In the positions shown at the foot of the support element, the leakage field generated by the large MRT magnet is small enough that a conventional ventilator motor 3 can be used.

The air line section 10 in this example is a flexible air hose 11. For example, provision can be made for the air hose 11 to be routed together with other cables which run from the stationary part into the moving part, i.e. from the support element 25 to the patient couch 24. The air hose can have a length of approximately 3 m and a maximum diameter of approximately 3 cm, for example. A larger diameter would possibly require substantial changes to the mechanism of the table or the patient couch 24 as opposed to a conventional design.

The air volume amplifier 4 may be adapted to the dimensions of the patient couch 24 or to that region of the patient couch in which the electronic components requiring ventilation are located. For example, the annular air volume amplifier 4 can have an outside diameter of approximately 5 cm.

Figure 7:
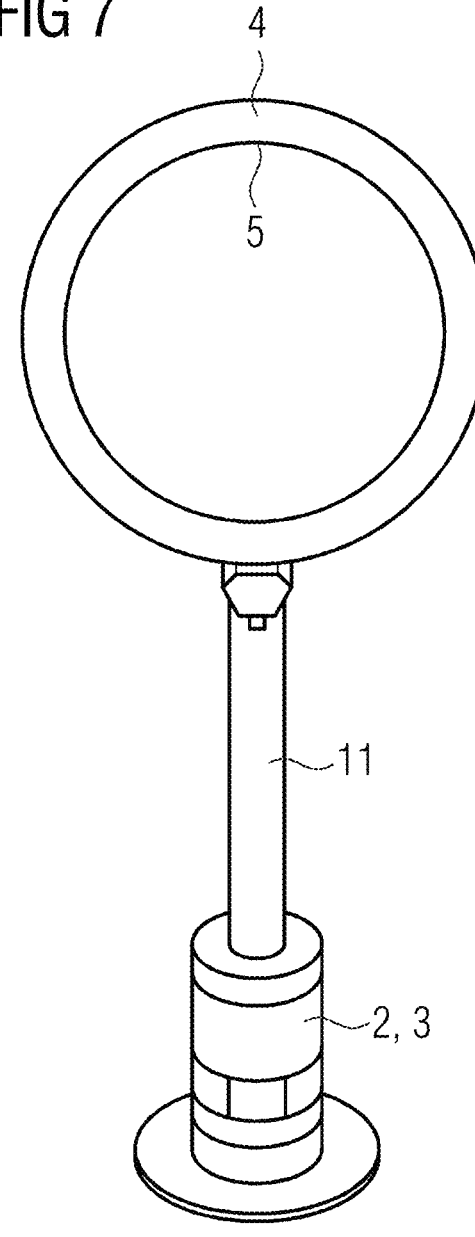
FIG. 7 shows a view of an adapted ventilator according to an exemplary embodiment of the disclosure.

FIG. 7 shows a view of an adapted ventilator according to an exemplary embodiment of the disclosure. The adapted ventilator may comprise an airstream generator 2 with a motor 3, and an annular air volume amplifier 4 which comprises an air exit 5 of the adapted ventilator. The adapted ventilator may also comprise an air line section 10 which carries an airstream that is generated by the airstream generator 2 to the air volume amplifier 4, where this airstream is amplified by the air volume amplifier 4 such that an airstream with increased air volume or an amplified airstream is generated. The air volume amplifier 4 may be made from a synthetic material and has no moving parts. The airstream is essentially amplified by the geometry of the air volume amplifier 4 and the air exit 5.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

The invention claimed is:

1. A magnetic resonance tomography system comprising:
a movable patient couch configured to be moved at least partially into an examination region of the magnetic resonance tomography system; and
an adapted ventilator including:
an air exit;
an airstream generator configured to generate an airstream;
an air volume amplifier arranged at the air exit and/or comprises the air exit, the air volume amplifier being configured to increase an air volume of the airstream, wherein the air volume amplifier is arranged and attached to the patient couch such that, in response to the patient couch being moved into the examination region, the air volume amplifier is moved into the examination region with the patient couch; and
an air line section configured to carry the generated airstream from the airstream generator to the air volume amplifier,
wherein the air volume amplifier is configured to increase an air volume of the airstream that is carried via the air line section to the air volume amplifier to output an amplified airstream with increased air volume.

2. The magnetic resonance tomography system as claimed in claim 1, wherein the air volume amplifier comprises a non-magnetic or non-magnetizable material and/or a non-conductive material.

3. The magnetic resonance tomography system as claimed in claim 1, wherein the air volume amplifier is configured to passively increase the air volume based on a geometric structure of the air volume amplifier.

4. The magnetic resonance tomography system as claimed in claim 1, wherein the air volume amplifier comprises an air-guiding annulus or annular section with air exit openings through which air is output in a direction having a directional component that is perpendicular to an annular plane.

5. The magnetic resonance tomography system as claimed in claim 1, wherein the air volume amplifier comprises an air-guiding annulus or annular section with air exit openings through which air is output in a direction that deviates by no more than 20° from a direction perpendicular to an annular plane.

6. The magnetic resonance tomography system as claimed in claim 1, wherein the airstream generator is arranged in a first region and the air volume amplifier is arranged in a second region, the first region having a lower magnetic field strength than the second region in response to the magnetic resonance tomography system generating a magnetic field during operation.

7. The magnetic resonance tomography system as claimed in claim 1, wherein the air volume amplifier is configured to amplify the air volume at least a factor of 5.

8. The magnetic resonance tomography system as claimed in claim 1, wherein the airstream generator is configured to input the airstream into the air line section with a pressure of 80 Pa to 500 Pa.

9. The magnetic resonance tomography system as claimed in claim 1, wherein the magnetic resonance tomography system further comprises an examination tunnel having a tunnel entrance, the air volume amplifier being arranged at the tunnel entrance and oriented such that the amplified airstream is directed into the examination tunnel along a longitudinal axis of the examination tunnel or is oriented such that the amplified airstream is directed out of the examination tunnel.

10. The magnetic resonance tomography system as claimed in claim 9, wherein the air exit of the air volume amplifier is arranged around a perimeter of the tunnel entrance and surrounds the tunnel entrance in an annular or partially annular manner.

11. The magnetic resonance tomography system as claimed in claim 1, wherein the air exit of the air volume amplifier is annularly shaped.

12. The magnetic resonance tomography system as claimed in claim 1, wherein the patient couch comprises an electronic component, the air volume amplifier being arranged such that the amplified airstream is directed at the electronic component.

13. The magnetic resonance tomography system as claimed in claim 12, wherein electronic component is a receiving coil.

14. The magnetic resonance tomography system as claimed in claim 1, wherein:
the magnetic resonance tomography system further comprises an examination tunnel having a tunnel entrance via which the patient couch is movable into the examination region that is arranged in the examination tunnel;
the magnetic resonance tomography system further comprises a support element arranged in front of the tunnel entrance, the patient couch being supported by resting on the support element when the patient couch is moved out of the examination tunnel; and
the airstream generator is arranged outside of the examination tunnel and positioned on the support element or integrated in the support element.

15. The magnetic resonance tomography system as claimed in claim 14, wherein the air line section between the airstream generator and the air volume amplifier is a flexible air hose.

16. A magnetic resonance tomography system comprising:
an examination tunnel having a tunnel entrance; and
a support configured to be arranged in front of the tunnel entrance and to support a patient couch; and
an adapted ventilator comprising:
an air exit;
an airstream generator configured to generate an airstream, wherein the airstream generator is arranged outside of the examination tunnel and positioned on the support or integrated with the support;
an air volume amplifier arranged at the air exit and/or comprises the air exit, the air volume amplifier being configured to increase an air volume of the airstream; and
an air line section configured to carry the generated airstream from the airstream generator to the air volume amplifier,
wherein the air volume amplifier is configured to increase an air volume of the airstream that is carried via the air line section to the air volume amplifier to output an amplified airstream with increased air volume.

17. The magnetic resonance tomography system as claimed in claim 16, wherein the air volume amplifier is arranged at the tunnel entrance and configured to: direct the amplified airstream into the examination tunnel or direct the amplified airstream out of the examination tunnel.

18. An adapted ventilator for a medical imaging device, comprising:

an air exit;

an airstream generator configured to generate an airstream;

an air volume amplifier arranged at the air exit and/or comprises the air exit, the air volume amplifier being configured to increase an air volume of the airstream; and an air line section configured to carry the generated airstream from the airstream generator to the air volume amplifier, the air volume amplifier being configured to increase an air volume of the airstream that is carried via the air line section to the air volume amplifier to output an amplified airstream with increased air volume, wherein:

the air volume amplifier is configured to amplify the air volume at least a factor of 5, or the airstream generator is configured to input the airstream into the air line section with a pressure of 80 Pa to 500 Pa.

* * * * *